(12) United States Patent
Anderson

(10) Patent No.: US 9,138,233 B2
(45) Date of Patent: Sep. 22, 2015

(54) APPARATUS AND METHOD FOR TISSUE ADHESION

(71) Applicant: MICROKOLL INC., Lompoc, CA (US)

(72) Inventor: Steven Craig Anderson, Lompoc, CA (US)

(73) Assignee: MICOKOLL INC., Lompoc, CA (US)

(*) Notice: Subject to any disclaimer, the term of this patent is extended or adjusted under 35 U.S.C. 154(b) by 0 days.

(21) Appl. No.: 14/531,656

(22) Filed: Nov. 3, 2014

(65) Prior Publication Data
US 2015/0051708 A1 Feb. 19, 2015

Related U.S. Application Data

(62) Division of application No. 13/119,540, filed on Mar. 17, 2011, now Pat. No. 8,906,046.

(51) Int. Cl.
| | |
|---|---|
| *A61B 17/08* | (2006.01) |
| *A61B 17/12* | (2006.01) |
| *A61B 17/00* | (2006.01) |
| *A61B 17/11* | (2006.01) |
| *A61F 2/848* | (2013.01) |
| *A61B 17/064* | (2006.01) |
| *A61F 2/00* | (2006.01) |

(52) U.S. Cl.
CPC ....... *A61B 17/12136* (2013.01); *A61B 17/0057* (2013.01); *A61B 17/064* (2013.01); *A61B 17/08* (2013.01); *A61B 17/11* (2013.01); *A61B 17/12113* (2013.01); *A61B 17/12131* (2013.01); *A61F 2/848* (2013.01); *A61B 17/0644* (2013.01); *A61B 2017/00668* (2013.01); *A61B 2017/00867* (2013.01); *A61B 2017/0641* (2013.01); *A61B 2017/0647* (2013.01); *A61B 2017/0649* (2013.01); *A61B 2017/1107* (2013.01); *A61B 2017/1132* (2013.01); *A61F 2/0063* (2013.01); *A61F 2002/0081* (2013.01); *A61F 2002/8483* (2013.01); *A61F 2210/0014* (2013.01); *A61F 2220/0016* (2013.01)

(58) Field of Classification Search
CPC ................ A61B 17/0057; A61B 2017/00575; A61B 2017/00592; A61B 17/12022; A61B 2014/00579; A61B 17/12136; A61M 25/104; A61M 25/10; A61M 2025/1052; A61M 2025/1075; A61F 2/958; A61F 2002/8483; A61F 2/848
See application file for complete search history.

(56) References Cited

U.S. PATENT DOCUMENTS

| | | | | |
|---|---|---|---|---|
| 4,485,816 | A * | 12/1984 | Krumme | 606/219 |
| 5,002,562 | A * | 3/1991 | Oberlander | 606/221 |
| 5,167,614 | A * | 12/1992 | Tessmann et al. | 623/1.15 |
| 5,246,443 | A * | 9/1993 | Mai | 606/78 |
| 5,634,936 | A * | 6/1997 | Linden et al. | 606/213 |
| 5,824,053 | A * | 10/1998 | Khosravi et al. | 623/1.15 |

(Continued)

*Primary Examiner* — Jonathan W Miles
(74) *Attorney, Agent, or Firm* — Felix F. Fischer

(57) ABSTRACT

An array of a plurality of shape memory material microposts have a proximal end configured to be secured to a substrate with a tissue penetrating distal end. The microposts further have a deployment state with the microposts in a substantially straightened configuration with a substantially smooth and continuous outer surface which is substantially parallel to adjacent microposts and an engaged state wherein at least a section of the microposts assume a configuration that is not substantially parallel to adjacent microposts or is not substantially straight with a substantially smooth and continuous outer surface so as to mechanically capture tissue adjacent thereto.

19 Claims, 17 Drawing Sheets

(56) References Cited

U.S. PATENT DOCUMENTS

| | | | |
|---|---|---|---|
| 5,843,167 A * | 12/1998 | Dwyer et al. | 623/1.14 |
| 5,968,053 A * | 10/1999 | Revelas | 606/108 |
| 6,695,878 B2 * | 2/2004 | McGuckin et al. | 623/1.19 |
| 6,712,836 B1 * | 3/2004 | Berg et al. | 606/213 |
| 8,241,308 B2 * | 8/2012 | Kortenbach et al. | 606/151 |
| 8,906,046 B2 * | 12/2014 | Anderson | 606/151 |
| 2001/0039434 A1 * | 11/2001 | Frazier et al. | 606/213 |
| 2002/0032481 A1 * | 3/2002 | Gabbay | 623/2.11 |
| 2002/0082641 A1 * | 6/2002 | Ginn et al. | 606/213 |
| 2003/0055491 A1 * | 3/2003 | Schwartz et al. | 623/1.21 |
| 2003/0093117 A1 * | 5/2003 | Saadat | 606/221 |
| 2003/0120330 A1 * | 6/2003 | Ouriel et al. | 623/1.12 |
| 2004/0064093 A1 * | 4/2004 | Hektner et al. | 604/103.01 |
| 2004/0073256 A1 * | 4/2004 | Marchitto et al. | 606/219 |
| 2004/0111100 A1 * | 6/2004 | Benderev et al. | 606/151 |
| 2004/0210282 A1 * | 10/2004 | Flock et al. | 607/96 |
| 2005/0033398 A1 * | 2/2005 | Seguin | 623/1.11 |
| 2005/0038470 A1 * | 2/2005 | van der Burg et al. | 606/213 |
| 2005/0192629 A1 * | 9/2005 | Saadat et al. | 606/221 |
| 2006/0190039 A1 * | 8/2006 | Birk et al. | 606/219 |
| 2007/0005092 A1 * | 1/2007 | Godin et al. | 606/194 |
| 2008/0103518 A1 * | 5/2008 | Karmon | 606/192 |
| 2008/0300610 A1 * | 12/2008 | Chambers | 606/159 |
| 2009/0054805 A1 * | 2/2009 | Boyle, Jr. | 600/564 |
| 2010/0179633 A1 * | 7/2010 | Solem | 623/1.11 |
| 2010/0249828 A1 * | 9/2010 | Mavani et al. | 606/213 |
| 2011/0034860 A1 * | 2/2011 | Melsheimer | 604/22 |

* cited by examiner

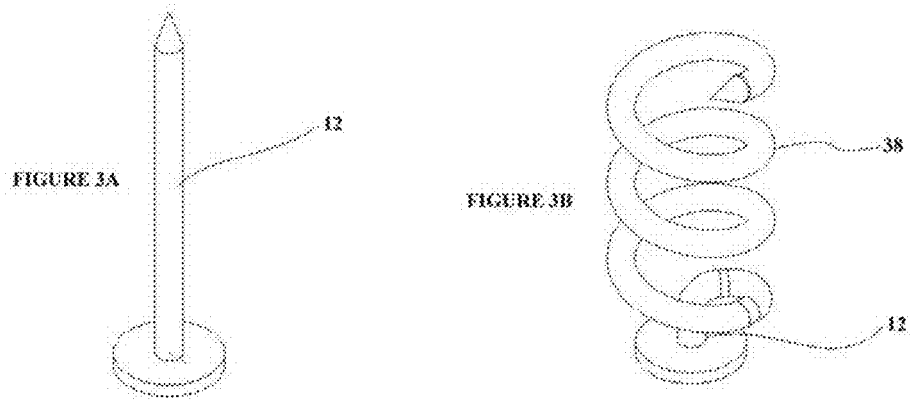
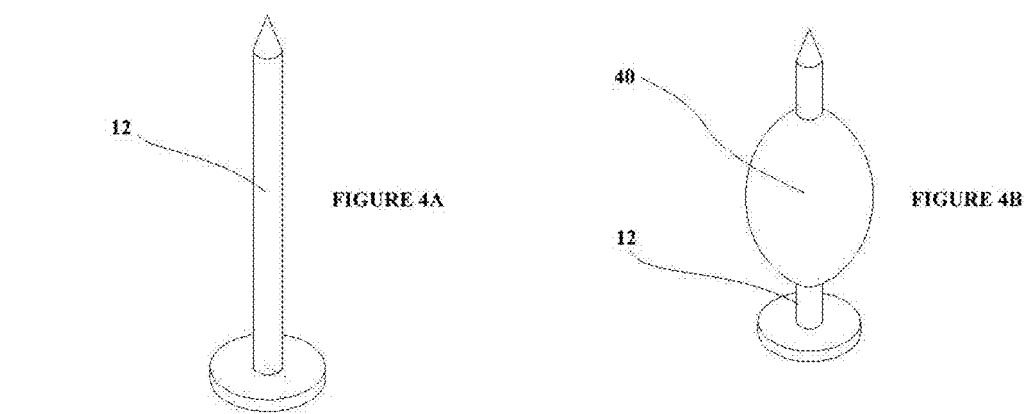
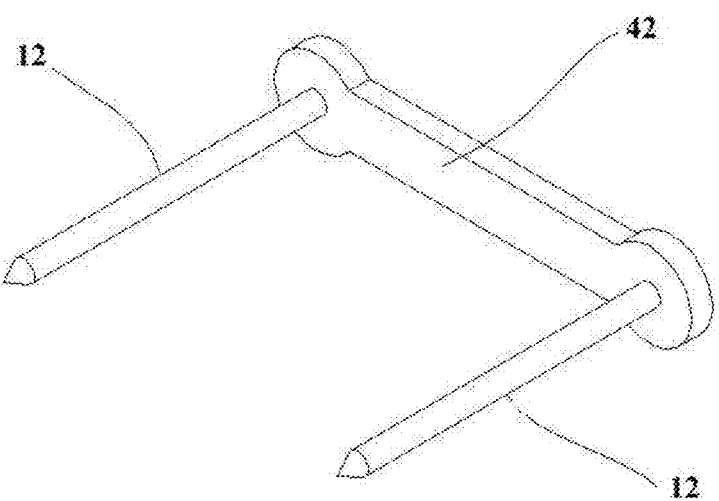
FIGURE 5

APPARATUS AND METHOD FOR TISSUE ADHESION

REFERENCE TO RELATED APPLICATIONS

This application is a divisional application of U.S. patent application Ser. No. 13/119,540 which is a national filing under 35 U.S.C. §371 of Patent Cooperation Treaty (PCT) application serial no. PCT/US2009/057348 having an international filing date of 17 Sep. 2009 claiming priority of U.S. provisional patent application Ser. No. 61192652 filed on 20 Sep. 2008 by inventor Steven Craig Anderson entitled APPARATUS AND METHOD FOR TISSUE ADHESION the disclosures of which are incorporated herein by reference.

BACKGROUND

1. Field

This application relates generally to the field of tissue modification and wound closure and more particularly to a substrate supporting a plurality of substantially parallel shape memory microposts for insertion into tissue adjacent a wound or tissue modification site with activation of the shape memory properties of the microposts to deform for adherence to the tissue.

2. Related Art

Tissue adhesion devices and methods have a wide variety of useful indications. For example, there is currently a need for surface adhesion to tissue for applications such as wound closure and anastomosis, which is the connection of two biological structures such as a vein graft to a coronary artery or the like. Current technologies to address such indications include the use of sutures, staples, or biological adhesives that may be used to join the two sections of tissue together. Each of these technologies has notable limitations. For example, a suture may be deployed into an incision, but tying and placing a proper knot in the suture may require a high degree of experience and manual dexterity and may be difficult for some operators. If the suture knot is not properly tightened, the incision may bleed or be otherwise compromised.

Some surgical staple embodiments may be deployed and secured by a variety of devices and mechanisms, such as by remote mechanical means, into an incision. Staples, however, may not always completely close the wound and may not be re-adjusted, if such adjustment is required, after deployment. In addition, staples tend to be deployed in discrete locations due to their bulk and may produce concentrated stress and strain points within tissue adjacent the deployed staples. Biological adhesives may be applied into a wound, but the presence of blood will often hinder an effectiveness of the adhesion strength between the adhesive and tissue. Also, biological tissue adhesives often tend to be rigid after they have cured, so as to cause stiffness at the point of contact and reduce flexibility of the wound when stress is applied thereto. Such a relatively stiff joint may even fracture or crack when stressed causing the wound to reopen and hemorrhaging to occur.

What has been needed are devices and methods for tissue adhesion that avoid these limitations. For example, tissue adhesion devices and methods that may hemostatically close an incision while remaining flexible such that an applied external stress will not damage the bond or joint would be highly desirable. It would be further desirable to provide devices that include a flexible surface or layer that may intimately attached or otherwise secured to tissue surfaces with a flexible joint.

SUMMARY

An embodiment incorporates an array of a plurality of microposts of shape memory material having a proximal end configured to be secured to the substrate and a tissue penetrating distal end. The microposts further have a deployment state with the microposts in a substantially straightened configuration with a substantially smooth and continuous outer surface which is substantially parallel to adjacent microposts and an engaged state wherein at least a section of the microposts assume a configuration that is not substantially parallel to adjacent microposts or is not substantially straight with a substantially smooth and continuous outer surface to mechanically capture tissue adjacent thereto.

In one configuration of the embodiment, a distal section of a micropost is curved back in the engaged state to mechanically capture tissue adjacent thereto in the deployed state. Such a capture can be accomplished wherein the distal end of the micropost is curved back such that a longitudinal axis of the distal end is at an angle of about 45 degrees to about 180 degrees from a nominal longitudinal axis of the micropost in the engaged state. In an alternative capture mechanism, capture is accomplished with a distal section of a micropost is bulged in the engaged state so as to mechanically capture tissue adjacent thereto in the deployed state. In yet another alternative capture mechanism, a distal section of a micropost assumes a corkscrew configuration in the engaged state to mechanically capture tissue adjacent thereto in the deployed state.

In certain configurations of the embodiments, the array of microposts employs a regularly spaced array while in other exemplary embodiments the array of microposts employs an irregularly spaced array.

For the disclosed embodiments, engagement of the microposts is accomplished through fabrication of the microposts with a shape memory material. Such shape memory materials may be a shape memory polymer or a shape memory alloy.

For various embodiments, the microposts may have an axial length of about 10 microns to about 1 mm and the microposts may have a transverse dimension of about 1 micron to about 0.5 mm Additionally, for the exemplary embodiments, the microposts have an inter-member spacing of about 10 microns to about 1 mm. The spacing is on the order of the axial length to twice the axial length depending on the engagement angle. In exemplary embodiments, if two microposts are facing each other, they will not touch after they are transitioned into the engaged state.

In one configuration, an angle of deflection of the distal end of the microposts in the engaged state is about 45 degrees to about 180 degrees from the nominal longitudinal axis of the tissue engagement member. In an alternative configuration, a radius of curvature is established in a distal section in the engaged state of about 100 percent to about 50 percent of the axial length of the respective microposts in the deployment state The microposts employed in certain embodiments have a substantially uniform axial length while in other embodiments, the microposts have differing axial lengths.

An exemplary embodiment provides a tissue adhesion patch which includes a flexible pad having a tissue interfacing contact surface with an array of microposts extending from the contact surface of the flexible pad. The microposts are a shape memory material having a proximal end secured to the flexible pad of material, a tissue penetrating distal end, a deployment state with the microposts in a substantially straightened configuration substantially parallel to adjacent microposts and an engaged state wherein a distal section of a tissue engagement member is curved back so as to mechanically capture tissue adjacent thereto. In an implementation of the embodiment, the array of microposts are integrally molded with a substrate which is attached to the pad tissue interfacing surface.

In one configuration of the patch embodiment, the distal end of the microposts is curved back to an angle of about 45 degrees to about 180 degrees from the nominal longitudinal axis of the tissue engagement member in the engaged state.

In an alternative configuration, the patch embodiment microposts have a radius of curvature in the engaged state that is about 100 percent to about 50 percent of the axial length of the respective microposts in the deployment state.

In the patch embodiment the microposts may have a longitudinal axis that is substantially perpendicular to a contact surface of the sheet of flexible material in the deployment state.

The embodiments provide a method of securing an object to tissue by the steps of advancing tissue penetrating distal ends of an array of microposts extending from and secured to a contact surface of the object into target tissue of a target tissue site. The microposts are then activated to transform from a deployment state with the microposts in a substantially straightened configuration having an outer surface which is smooth, continuous and substantially parallel to adjacent microposts to an engaged state wherein at least a section of the microposts assume a configuration that is not substantially parallel to adjacent microposts or is not substantially straight with a substantially smooth and continuous outer surface to mechanically capture tissue adjacent thereto.

In one form to accomplish the method, the distal sections of the microposts are curved back in the engaged state so as to mechanically capture tissue adjacent thereto in the deployed state.

In a second form to accomplish the method, the distal sections of the microposts are bulged in the engaged state so as to mechanically capture tissue adjacent thereto in the deployed state.

In a third form to accomplish the method, the distal sections of the microposts assume a corkscrew configuration in the engaged state so as to mechanically capture tissue adjacent thereto in the deployed state.

In various implementations of the method the microposts are activated thermally, by passage of electrical current through the microposts, by a change in the pH value of the material surrounding the microposts, by the application of light energy to the microposts, or by the application of ultrasonic energy to the microposts.

Using an exemplary embodiment provides a method for wound closure or occluding a body passageway or body cavity by advancing tissue penetrating distal ends of an array of microposts extending from and secured to a contact surface of flexible sealed balloon which can be inflated and deflated placed into target tissue surrounding a wound or in the passageway or cavity to be occluded. The balloon is inflated and the microposts activated to transform the microposts from a deployment state with the microposts in a substantially straightened configuration having an outer surface which is smooth and continuous and substantially parallel to adjacent microposts to an engaged state wherein at least a section of the microposts assume a configuration that is not substantially parallel to adjacent microposts or is not substantially straight with a substantially smooth and continuous outer surface to mechanically capture tissue adjacent thereto. The balloon is then deflated. The balloon incorporates an internal sealing mechanism which secures the inner walls of the balloon to itself thus closing the wound or occluding the body passageway or cavity.

In one configuration of the wound closing balloon embodiment the internal sealing mechanism is Velcro. In a second configuration, the internal sealing mechanism is an adhesive.

Using an alternative exemplary embodiment provides a method of performing an anastomosis by advancing tissue penetrating distal ends of an array of microposts extending from and secured to a contact surface of the outer surface of a flexible tube into target tissue of a target tissue site. The flexible tube is inserted into both sides of an anastomosis connection. The tube is expanded in order to deploy the microposts. The microposts are activated to transform the microposts from a deployment state with the microposts in a substantially straightened configuration having an outer surface which is smooth and continuous and substantially parallel to adjacent microposts to an engaged state wherein at least a section of the microposts assume a configuration that is not substantially parallel to adjacent microposts or is not substantially straight with a substantially smooth and continuous outer surface so as to mechanically capture tissue adjacent thereto thus securing the flexible tube into both sides of the anastomosis.

The embodiments may also provide a method of securing an implantable device to tissue using an array of microposts extending from and secured to a contact surface of an implantable device via the use of a substrate coating on the implantable device on which the microposts are formed. The microposts are advanced with tissue penetrating distal ends of the array of into target tissue of a target tissue site. The microposts are activated to transform the microposts from a deployment state with the microposts in a substantially straightened configuration having an outer surface which is smooth and continuous and substantially parallel to adjacent microposts to an engaged state wherein at least a section of the microposts assume a configuration that is not substantially parallel to adjacent microposts or is not substantially straight with a substantially smooth and continuous outer surface to mechanically capture tissue adjacent thereto. The implantable device is deployed into the target area, and the microposts are deployed into the tissue and engaged by activation of the shape memory material thus securing the device to the tissue.

The features, functions, and advantages that have been discussed can be achieved independently in various embodiments of the present invention or may be combined in yet other embodiments further details of which can be seen with reference to the following description and drawings.

BRIEF DESCRIPTION OF THE DRAWINGS

FIG. 3A is a perspective view of an alternative embodiment of a micropost in an deployment state;

FIG. 3B is a perspective view of the embodiment of FIG. 3A in the engaged state;

FIG. 4A is a perspective view of a second alternative embodiment of a micropost in an deployment state;

FIG. 4B is a perspective view of the embodiment of FIG. 4A in the engaged state;

FIG. 5 is a perspective view of a shape memory material insert with two micropost extending therefrom in the deployment state;

DETAILED DESCRIPTION

Figure 1A:
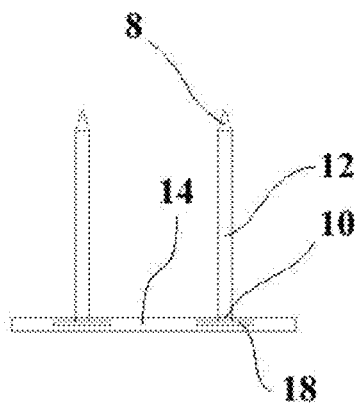
FIG. 1A is a side view of a first embodiment having a sheet of flexible material with an array of a plurality of microposts extending therefrom in an engagement state.
Figure 1B:
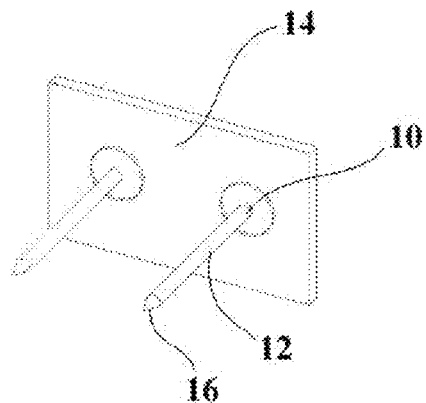
FIG. 1B is a perspective view of the embodiment of FIG. 1A

Embodiments of the invention include a composite structure with a flexible sheet or substrate and a plurality of substantially parallel shape memory microposts secured thereto. For some embodiments, the microposts may be integral with the substrate. The substrate may serve to confine and position the shape memory microposts for some embodiments as generally illustrated in FIGS. 1A and 1B. FIG. 1A shows the proximal end 10 of a pair of microposts 12 secured to a substrate 14. For the embodiment shown in the drawings, the proximal end incorporates a lateral flange 16 for engagement within the substrate to resist extraction. The microposts have a sharpened distal end 18. Because the substrate may be flexible or elastomeric, it may have the ability to conform to any irregular surface that it is forced against. For the embodiments shown in the drawings a circular cross section for the microposts is shown. In alternative embodiments, a non-circular cross section may be employed. The device is deployed by applying pressure to the underside of the flexible substrate which forces the sharpened distal ends 18 of the shape memory microposts 12 into the target tissue. The shape memory microposts may be fabricated from a polymer material for some embodiments, and the microposts may be configured to have a substantially straightened deployment state 12. The microposts may also be configured to have an engaged state 12' wherein distal sections of the microposts have been activated so as to take on a shape which engages the adjacent tissue into which the micropost has been inserted. Various shapes such as a curved or hooked shape (as shown and described subsequently in FIG. 2D) that are configured to mechanically capture tissue adjacent thereto may be employed.

Memory activation of distal sections of the microposts may be triggered by any suitable means for a respective micropost embodiment. Shape memory members that are in the deployment state can be transitioned into the engaged state through a variety of methods which depend on the nature of the shape memory material. For some embodiments, the device may be configured to produce high strength adhesion properties with minimal tissue damage or engagement by virtue of using a large number of short thin tissue penetration members closely spaced together.

Figure 1C:
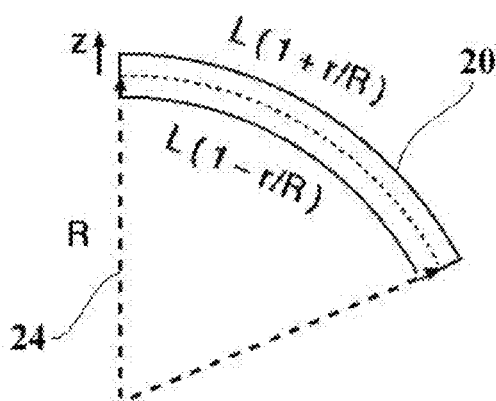
FIG. 1C illustrates the angular deflection of a section of a micropost.
Figure 1D:
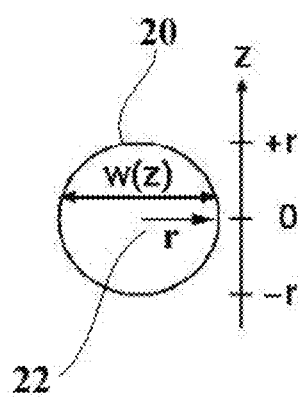
FIG. 1D shows a cross section of a micropost for purposes of defining the cross sectional shape function $W(z)$.

An analysis of the force to bend a thin rod or micropost through a given radius of curvature is provided as exemplary of the adhesion properties of some device embodiments which then allows for the determination of the theoretical attachment force of the microposts to tissue. Referring to FIGS. 1C and 1D, r is the radius 22 of a rod 20 and R is the radius of curvature 24 of the bent rod. It is assumed that r<<R. The elastic bending energy per unit length of the rod is given by:

$$\frac{Ebend}{L} = \int_{-r}^{r} 2 \cdot (r^2 - z^2) \cdot Y \cdot \frac{(z/r)2}{2} \cdot dz$$

Using a change of variables, x=z/r:

$$\frac{Ebend}{L} = \frac{2 \cdot Y \cdot r^4}{R^2} \cdot \int_{-1}^{1} x^2 \cdot (1-x^2)^{1/2} \cdot dx \text{ where}$$

$$\int_{-1}^{1} x^2 \cdot (1-x^2)^{1/2} \cdot dx = \frac{\pi}{8}$$

The resulting equation provides $$\frac{Ebend}{L} = \frac{Y \cdot r^4}{R^2} \cdot \left[\frac{\pi}{8}\right] = \frac{Y}{2 \cdot R^2} \cdot \left[\frac{1}{4} \cdot \pi \cdot r^4\right] = \frac{Y \cdot I}{2 \cdot R^2} \quad (1)$$

Equation (1) provides the force to deflect a thin rod to a radius of curvature R. If the diameter of the micropost is 2 microns, and the length of the micropost is 12 microns, the second moment area of inertia for a circular cross section may be given by:

$$I = \frac{\pi \cdot D^4}{64} = \frac{\pi \cdot (2 \cdot 10^{-6} m)^4}{64} = 7.85 \cdot 10^{-25} m^4$$

For this example, a polyurethane shape memory polymer with a flexural modulus of 1100 MPa will be used for the rod material. Per FIG. 1C the radius of curvature of the engagement member may be approximately equal to the length of the micropost. Thus equation (1) may be rewritten as:

$$F_{rod} = \frac{Y \cdot I}{2 \cdot R^2} = \frac{1100 \cdot 10^6 \text{Pa} \cdot 7.85 \cdot 10^{-25} m^4}{2 \cdot (12 \cdot 10^{-6} m)^2} = 3.00 \cdot 10^{-6} N$$

$F_{rod}$ is the force required to bend one micropost to a radius of curvature that is equal to its length. Now, consider an array of microposts secured to a flexible substrate sheet. Assuming that the microposts are spaced 12 microns apart from adjacent microposts as tissue engagement members (for an exemplary embodiment as shown and discussed subsequently with respect to FIGS. 12A and 12B). The surface area of flexible substrate surrounding one micropost can be:

$$A = (12 \cdot 10^{-6} m) \cdot (12 \cdot 10^{-6} m) = 1.44 \cdot 10^{-10} m^2$$

Therefore, in one square meter of flexible substrate, there may be about:

$$\frac{1 m^2}{1.44 \cdot 10^{-10} m^2} = 6.94 \cdot 10^9 \text{ Microposts}$$

The tensile force that each activated tissue engagement member can resist prior to tissue disengagement is known and is shown above as $F_{rod}$. The total number of members is multiplied by the force per member to yield the strength of the substrate attachment (per square meter):

$$6.94 \cdot 10^9 \text{ Microposts} \cdot \frac{3.00 \cdot 10^{-6} N}{\text{Micropost}} \cdot \frac{1}{1 m^2} = 20,800 \text{ Pa} = 20.8 kPa$$

Figure 2A:
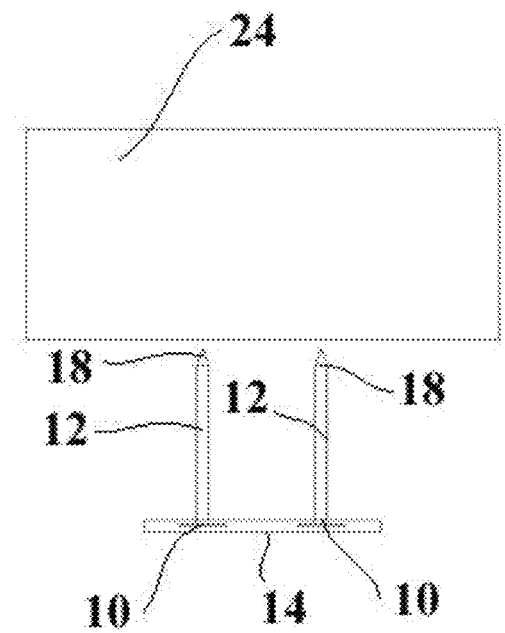
FIGS. 2A-2D illustrate a deployment sequence for the embodiment of FIGS. 1A and B.
Figure 2B:
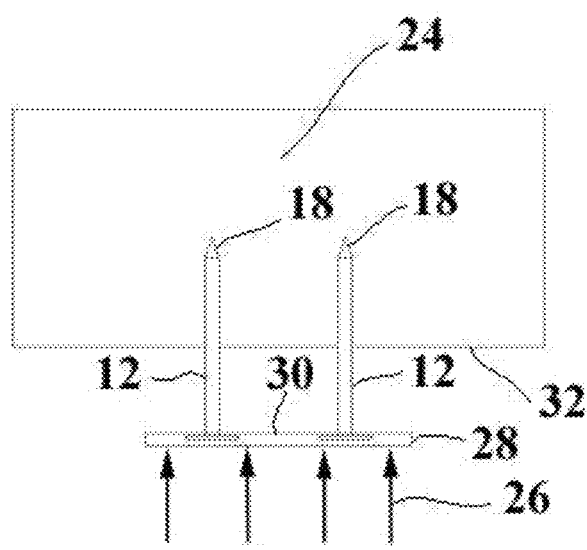
Figure 2C:
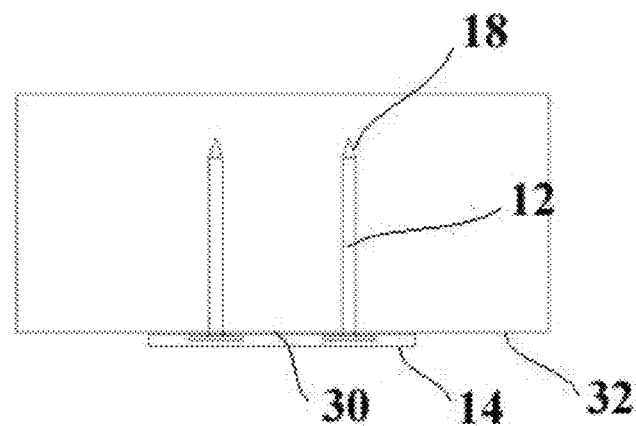
Figure 2D:
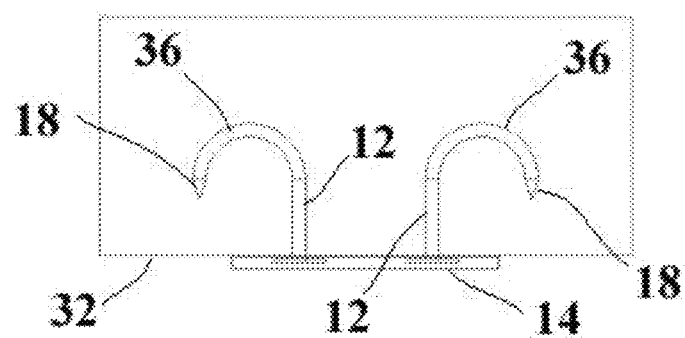

Deployment of the embodiment of a system as described with respect to FIGS. 1A and 1B is shown in FIGS. 2A-2D. In FIG. 2A, distal ends 18 of the microposts are in the deployment state with each micropost 12 being substantially parallel to adjacent microposts with substantially straight smooth and continuous outer surfaces. The substrate 14 is secured to the proximal ends 10 of the microposts 12 by the lateral flanges 16. In FIG. 2B, the microposts have been partially deployed and are shown with distal tips 18 thereof penetrating into the target tissue 26 via pressure, generally shown as arrows 34, applied to outer surface 28 of the substrate which is opposite to inner surface 30 from which the microposts extend. In FIG. 2C, the tissue engagement microposts have been fully deployed into the target tissue 26 by pressure on the underside of the substrate sheet such that the inner surface 30 of the substrate 14 is in contact with an outer surface 32 of the target tissue and substantially all of the microposts of the system are disposed within and surrounded by target tissue. In FIG. 2D, the microposts have been activated to an engaged state 12' such that distal sections of the microposts have assumed a shape that mechanically captures tissue adjacent to each micropost between the micropost and the substrate and binds the substrate to the tissue. Through this process, the substrate is mechanically secured to the target tissue by the microposts.

For some embodiments this activation mechanism may also serve to pull the substrate 14 tightly against the outer surface 32 of the target tissue 26 due to the curling or hooking movement of the distal section of the microposts. The micropost embodiments shown in FIGS. 2A-2D are curved back when activated in order to mechanically capture tissue adjacent thereto in the activated or engaged state represented as element 12'.

Another embodiment of microposts may include a corkscrew configuration shown in FIGS. 3A and 3B. The deployment sequence for this embodiment may be as follows. The micropost 12 is straight, smooth, and parallel to any adjacent microposts in its deployment state as shown in FIG. 3A. After the micropost has been deployed or otherwise disposed into the target tissue, it is activated and a distal section 38 of the micropost assumes its corkscrew shape thus capturing tissue between successive rotations of the micropost so as to anchor the micropost in the target tissue in an axial direction as shown in FIG. 3B.

Yet another embodiment of a tissue engagement member may include a distal section that is bulged in the activated state so as to mechanically capture tissue as is shown in FIGS. 4A and 4B. The deployment sequence for this embodiment might be as follows. The micropost 12 is straight, smooth, and parallel to adjacent microposts in its deployment state. As shown in FIG. 4A After the micropost has been deployed or otherwise disposed into the target tissue, it is activated and a portion 40 of the distal section assumes its bulged shape thus capturing tissue between bulged distal section and the proximal section of the micropost as shown in FIG. 4B.

Figure 6:
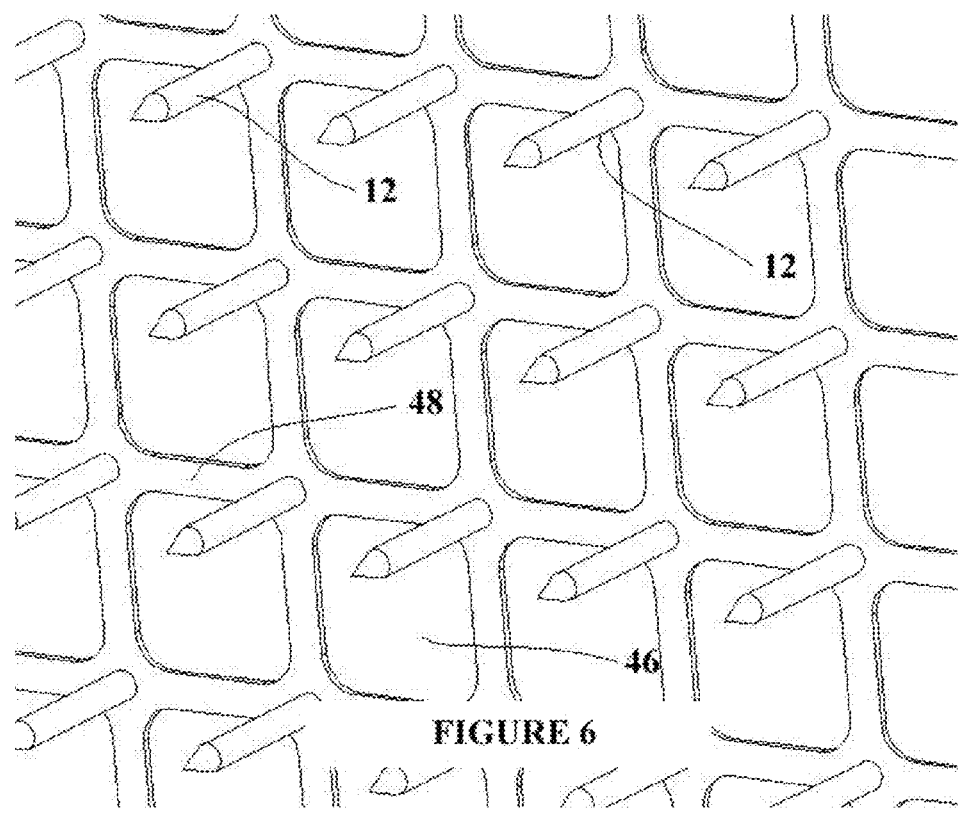
FIG. 6 is a perspective view of a sheet of shape memory material with an array of a plurality microposts extending therefrom in a deployment state.

Other possible tissue micropost embodiments may include microposts 12 that are formed as a single element from shape memory material with a ribbon or strip 42 at a base 44 of each micropost to form a pair as shown in FIG. 5. This embodiment may aid in the attachment of the microposts to the flexible substrate. In yet another embodiment, an array 46 of the microposts 12 might be integrally molded from shape memory material with a plurality of connecting strips 48 as shown in FIG. 6. This embodiment may be beneficial for manufacturing purposes in that holding and positioning small microposts during the flexible base over molding process would be difficult. The insert configuration in FIG. 6 could also be used as a stand alone apparatus that could be deployed into tissue in order to provide structural support for that tissue. The gaps between the connecting strips 48 could act as ports for tissue drainage.

For some embodiments, the substrate sheet may be fabricated from any suitable flexible material such as the following elastic polymers: silicone rubber, polyurethane, or latex rubber. Embodiments of microposts may be fabricated from any suitable shape memory alloy or shape memory polymer. Like their counterparts in metallic shape memory metals, shape memory polymers experience "memory" effects which allow them to recover a pre-determined shape after a transitional event has occurred. Some shape memory polymers may include polyurethane, polystyrene, polynorbornene, and a variety of hydrogels. It may be desirable for some embodiments for both the substrate and the microposts to be made from bio-absorbable material. Various metals and alloys with shape memory properties may be used in various embodiments of microposts including but not limited to NickelTitanium (NiTi).

For the general embodiments of the microposts shown in FIGS. 2A-2D NiTi alloys with thermal activation may be employed for certain applications. Alternatively, polymer microposts with either thermal, electrical, or photonic activation may be employed. Polymers such as polyurethane doped with carbon nanotubes provide electrical conductivity for shape memory activation. Polymers may also be employed with shape memory activation through exposure to Ultraviolet (UV) radiation. Alteration of the pH of the polymer may also activate the shape memory property by exposure to acidic or base fluids in the tissues or in which the tissues are bathed or, alternatively, by removing the polymer from a stabilizing fluid and allowing change of pH through insertion in to the tissue.

Figure 7A:
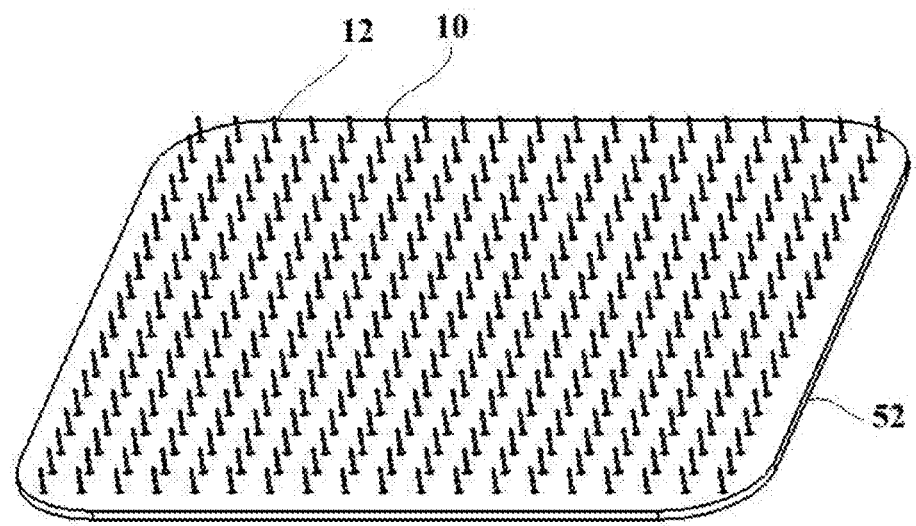
FIG. 7A illustrates an embodiment of a pad device having an array of a plurality of microposts for deployment within tissue.
Figure 7B:
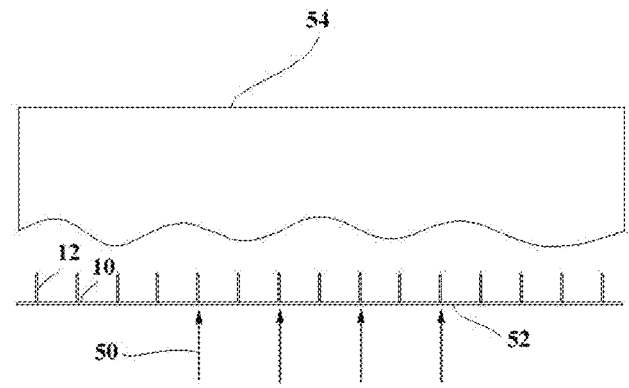
FIGS. 7B, 7C and 7D illustrate a deployment sequence of the embodiment of the pad device of FIG. 7A into tissue with engagement.
Figure 7C:
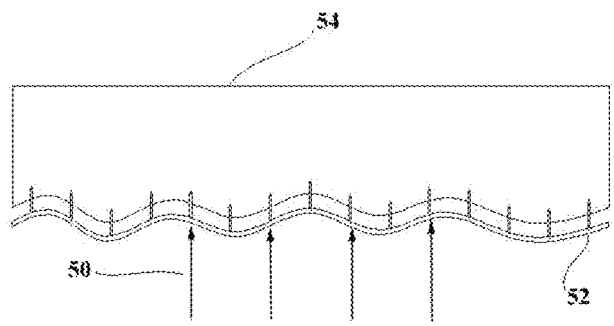
Figure 7D:
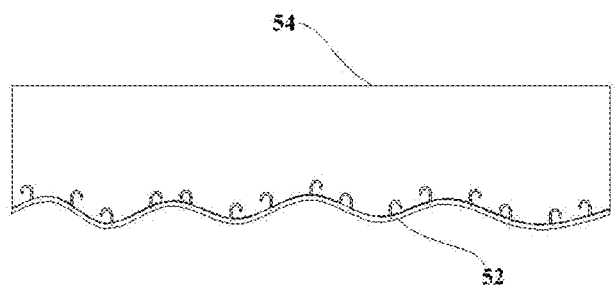

FIG. 7A shows an embodiment of with a substrate sheet 50 and micropost array 46 having a structure such as that shown in FIG. 6 integrated as a pad 52. In an exemplary embodiment, the substrate 50 may be molded around the connecting strips 48 to secure the entire array to form the pad 52. In another embodiment, the substrate 50 may be molded around a plurality of the connecting strips 42 of the composite micropost shown in FIG. 5 to form the array contained within the pad 52. In yet another embodiment, the substrate 50 may be molded around the lateral flanges 16 of multiple microposts as shown in FIGS. 1A and 1B to form the array contained within the pad 52. The scale of the microposts is exaggerated in the figures for the embodiments to allow visualization in the drawings where in actual embodiments, the micorposts would be much smaller in relation to the other drawing elements. The microposts are arranged on one interface surface of the pad to allow for attachment to a suitable tissue surface by that side of the pad. The pad system of FIG. 7A may include a variety of embodiments wherein the microposts are activated by different methods. The pad would be attached to any suitable target tissue using the following exemplary method as described with respect to FIGS. 7B and 7C. The pad 52 would be placed in contact with the target tissue 54 such that the distal tips 18 of the microposts 12 were contacting the target tissue. Pressure represented generally by arrows 56 may then be applied to the underside 58 of the pad thus deploying it into the target tissue, as shown in FIG. 7C. The microposts 12 would then be transitioned to the engaged state 12' by any suitable method thus securing the pad to the target tissue as shown in FIG. 7D to secure the tissue similar to the sequence shown in FIGS. 2A-2D and discussed above.

For the exemplary embodiment of FIG. 7A a NiTi alloy may be employed as the shape memory material for the microposts. The pad is maintained at a reduced temperature (approximately 26C or lower) prior to use. Deployment of the pad onto the tissue results in warming of the microposts to the temperature of the body (approximately 38C) which is sufficient to thermally activate the shape memory properties of the NiTi microposts. In this case the NiTi material has an activation temperature of 38C. Below this temperature the NiTi material is in its Martensite state which corresponds to the deployment state of the shape memory micropost. Above this temperature the NiTi material is in its Austenite state which corresponds to the engagement state of the shape memory micropost.

Figure 8A:
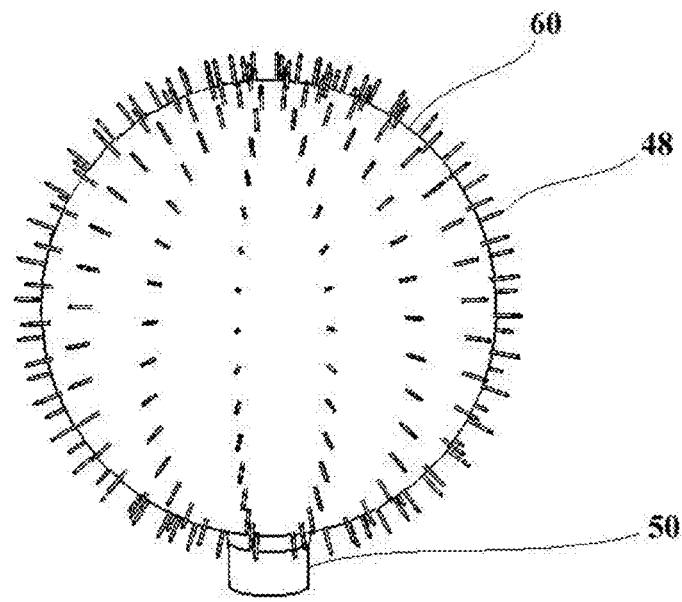
FIG. 8A illustrates an embodiment of a balloon device having an array of a plurality of microposts for engagement within tissue.
Figure 8B:
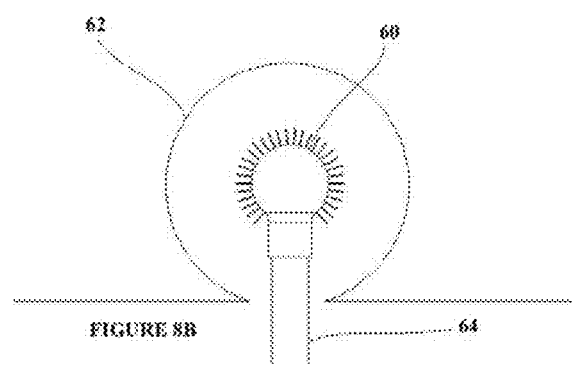
FIGS. 8B-8F illustrate a deployment sequence of the embodiment of the balloon device of FIG. 8A for occlusion of an aneurysm.
Figure 8C:
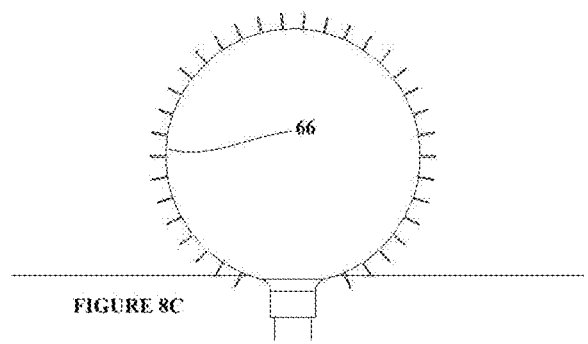
Figure 8D:
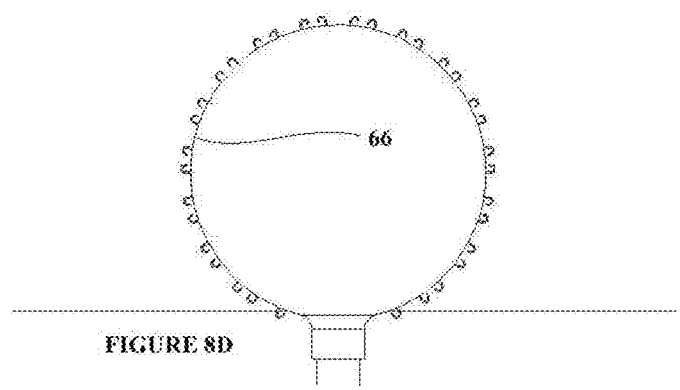
Figure 8E:
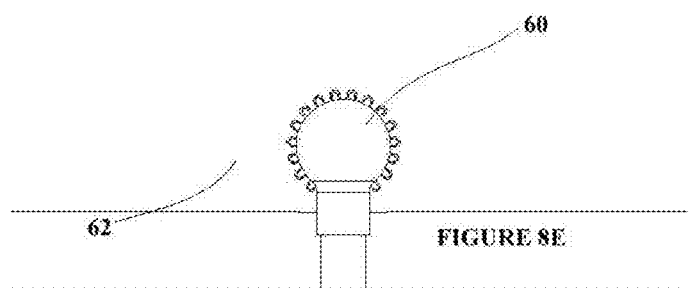
Figure 8F:
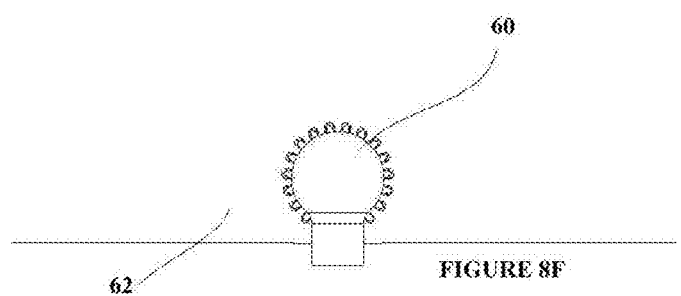

FIG. 8A shows an embodiment of the substrate sheet 50 and micropost array 46 configured as a balloon 60. The microposts are arranged on the outside surface of the balloon so as to allow for attachment to a suitable tissue surface by that side of the balloon. The substrate is elastically expandable for inflation of the balloon. The balloon system of FIG. 8A may include a variety of embodiments wherein the microposts are activated by different methods. The balloon may be attached to any suitable target tissue according to the following method as described with respect to FIGS. 8B-8F. The balloon 60 may be placed into the proximity of the target tissue 62 (in this case the aneurysm shown in FIG. 8B) using a catheter shaft 64 or similar device and then the balloon would be inflated thus deploying the microposts into the target tissue as shown in FIG. 8C. The microposts 12 would then be transitioned to the engaged state 12' by any suitable method thus securing the balloon to the target tissue as shown in FIG. 8D in a process similar to the sequence shown in FIGS. 2A-2D and discussed above. The balloon may then be deflated and sealed upon itself via self-adhering internal surfaces 66 (shown in FIG. 8D) as shown in FIG. 8E. The balloon would then detach from the catheter shaft 64 as shown in FIG. 8F. Internal sealing of the balloon may be accomplished using an internal sealing mechanism such as mating Velcro® sheets. Alternatively, an adhesive may coat the internal surface of the balloon or be introduced through the catheter during inflation of the balloon.

Figure 9A:
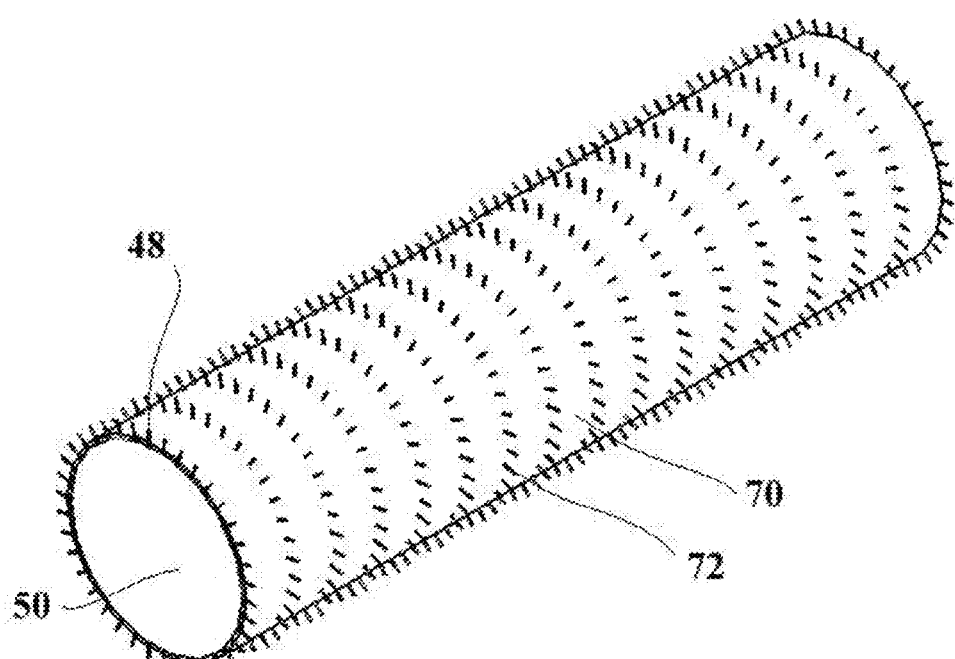
FIG. 9A illustrates an embodiment of a tube device having an array of a plurality of microposts for engagement within tissue.
Figure 9B:
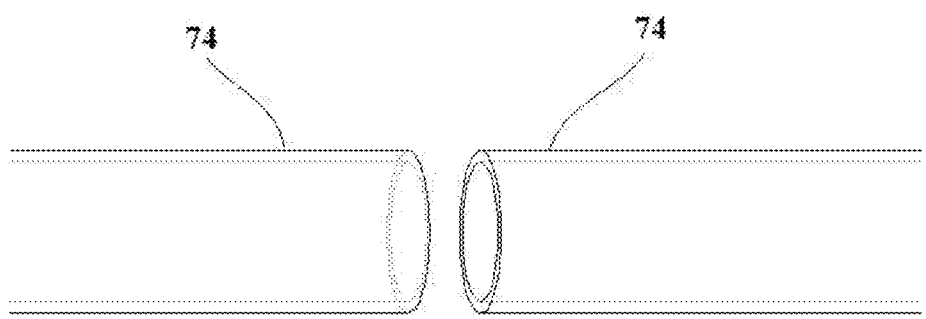
FIGS. 9B-9E illustrate a deployment sequence of the embodiment of the balloon device of FIG. 9A within a patient's vasculature in order to perform an anastomosis.
Figure 9C:
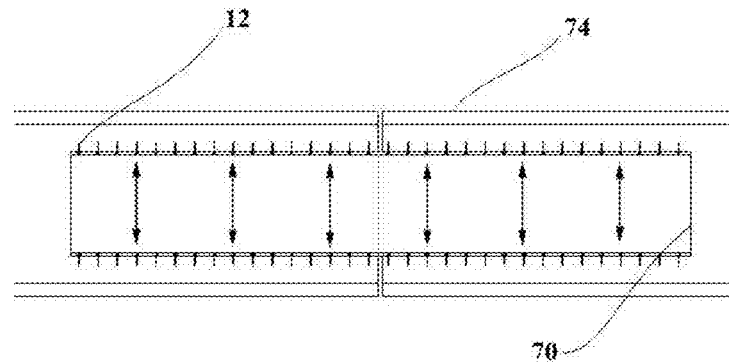
Figure 9D:
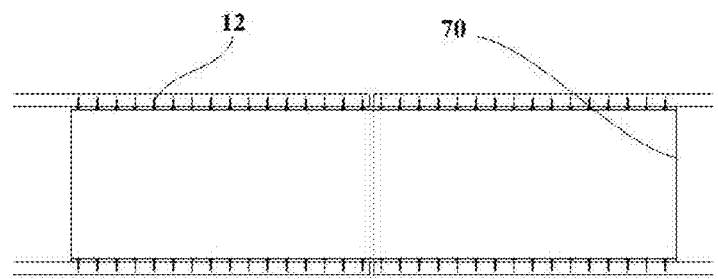
Figure 9E:
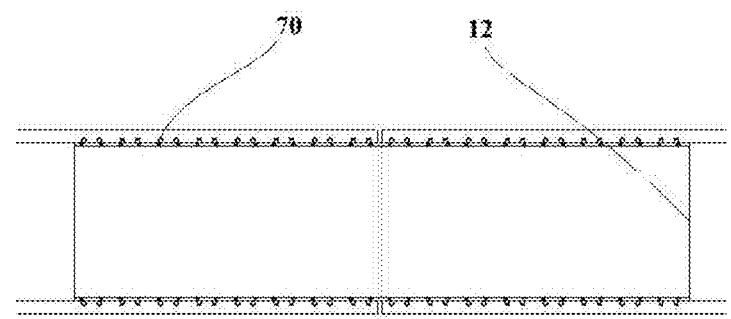

FIG. 9A shows an embodiment of the substrate sheet 50 and micropost array 46 configured as a tube 70. The microposts are arranged on the outside surface 72 of the tube so as to allow for attachment to a suitable tissue surface by that side of the tube. The tube system may include a variety of embodiments wherein the microposts are activated by different methods. The tube may be attached to any suitable target tissue (in this case the anastomosis vessels 74 shown in FIG. 9B) according to the following method described with respect to FIGS. 9C-9E. The tube 70 may be placed into the proximity of the target tissue such as vessels 74 as shown in FIG. 9C and then the tube may be expanded radially via internal pressure 76 thus deploying the microposts 12 into the target tissue as shown in FIG. 9D. The microposts 12 would then be activated to the engaged state 12' by any suitable method thus securing the tube 70 to the target tissue as shown in FIG. 9E.

Figure 10A:
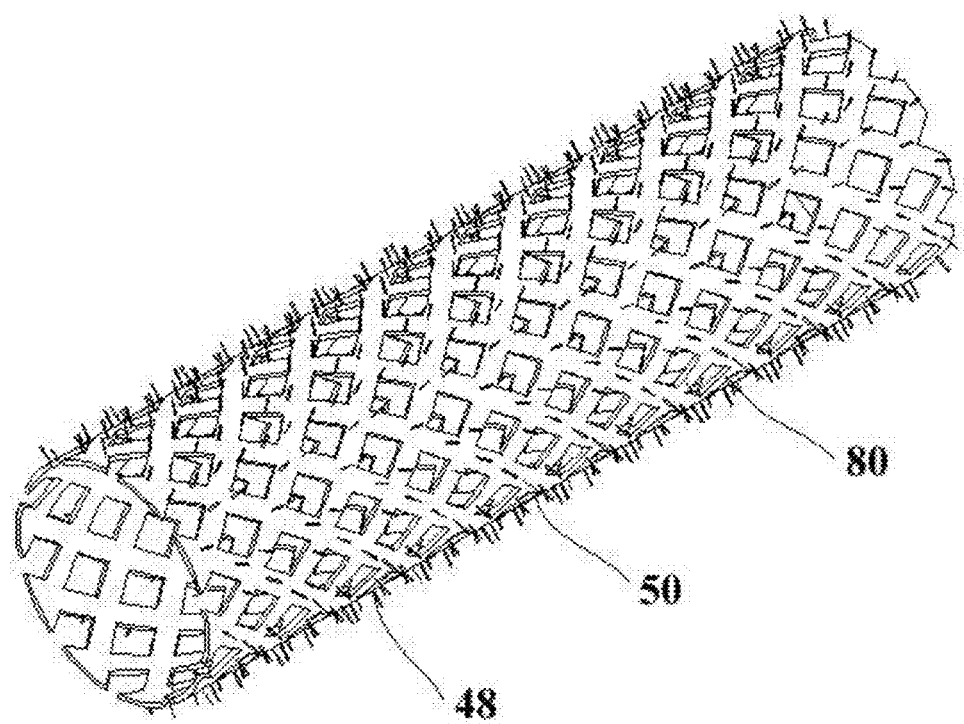
FIG. 10A illustrates an embodiment of a stent device having a coating consisting of an array of a plurality of microposts for engagement within tissue.
Figure 10B:
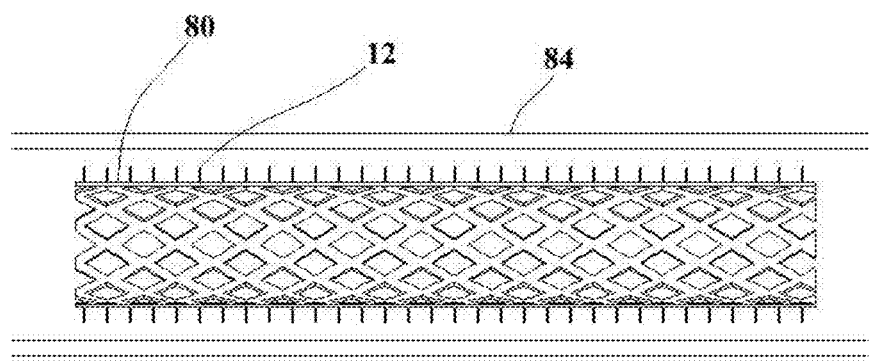
FIGS. 10B-10D illustrate a deployment sequence of the embodiment of the coated stent device of FIG. 10A within a patient's vasculature.
Figure 10C:
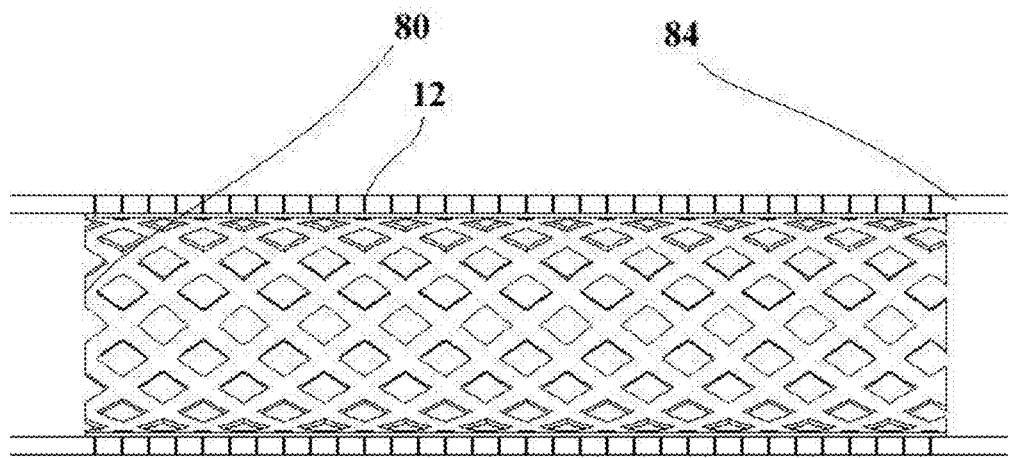
Figure 10D:
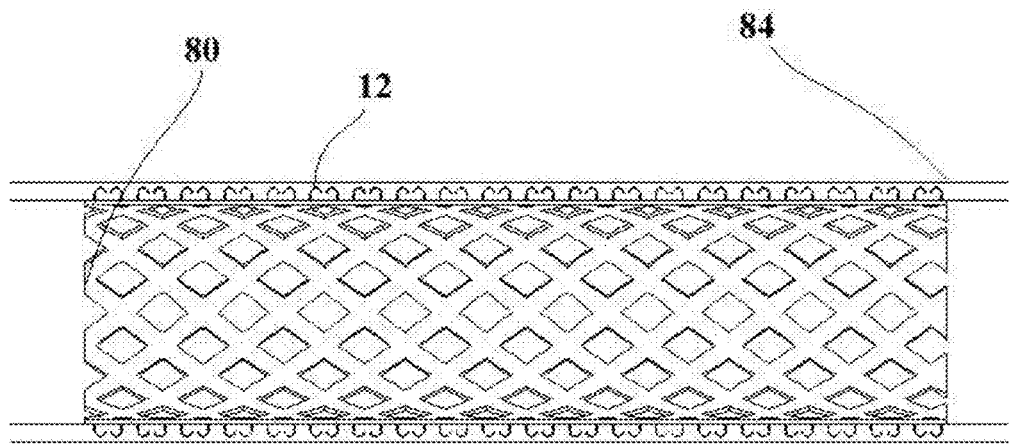

FIG. 10A shows an embodiment of the substrate sheet 50 and micropost array 46 configured as a coating on an implantable device, in this case a intravascular stent 80. The coating is applied such that the microposts are arranged on the outside surface of the stent 82 to allow for attachment to a suitable tissue surface by the stent. The stent system of FIG. 10A may include a variety of embodiments wherein the microposts are activated by different methods. The stent may be attached to any suitable target tissue according to the following method as described with respect to FIGS. 10B-10D. The stent 80 may be placed into the proximity of the target tissue 84 as shown in FIG. 10B and then the stent may be expanded radially via internal pressure 86 thus deploying the microposts 12 into the target tissue as shown in FIG. 10C. The microposts 12 may then be transitioned to the engaged state 12' by any suitable method thus securing the stent 80 to the target tissue 84 as shown in FIG. 10D.

Figure 11A:
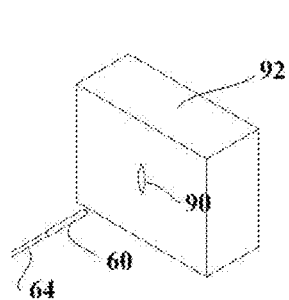
FIGS. 11A-11E illustrate a deployment sequence of a balloon device such as the embodiment of FIG. 8A for closure of a wound.
Figure 11B:
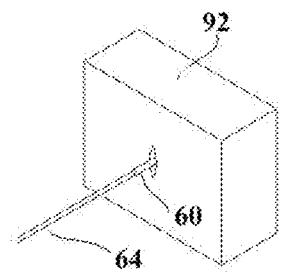
Figure 11C:
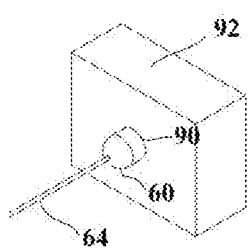
Figure 11D:
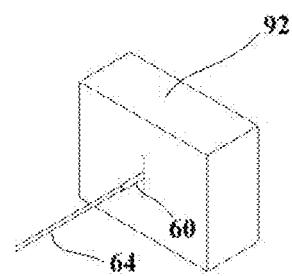
Figure 11E:
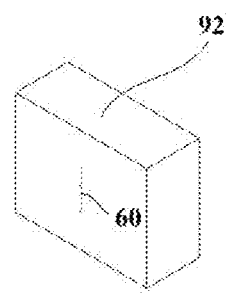

FIGS. 11A-11E illustrate a deployment sequence of a wound closure method employing the embodiment described above with respect to FIG. 8A. The figures depict an inflatable balloon 60 which has microposts extending radially therefrom being used to close a wound. The balloon system of FIGS. 11A-11E may include a variety of embodiments wherein the microposts are activated by different methods. Embodiments of the balloon may also include another feature that serves to hold the collapsed balloon closed once the microposts have been activated and the balloon collapsed. For some embodiments, the internal surfaces of the balloon may include self-adhering surfaces such as adhesive coated surfaces, Velcro® surfaces or the like. When a negative pressure is applied and the balloon is deflated, the interior surfaces would lock together thus sealing the balloon providing tissue closure. Referring again to FIGS. 11A-11E, for any of the balloon embodiments discussed above, the catheter or shaft having the balloon 60 disposed thereon is advanced into a wound 90 in the target tissue 92 in a collapsed state such that the microposts are disposed adjacent tissue to be closed as shown in FIG. 11B. Once properly positioned, the balloon may then be expanded such that the microposts are expanded radially outward towards the extent of the wound 90 in the target tissue and the tissue penetrating tips of the microposts penetrate the target tissue as shown in FIG. 11C. The microposts may then be activated by any of the methods discussed herein so as to secure the balloon substrate to the target tissue so as to secure the tissue similar to the sequence shown in FIGS. 2A-2D and discussed above. Once the microposts have been activated and secured to the target tissue, the balloon may be collapsed so as to draw the wound closed as shown in FIG. 11D. The balloon may then be detached from the catheter shaft by cutting or any other suitable method and the catheter shaft withdrawn from the target tissue as shown in FIG. 11E. Elastomeric balloons, such as those discussed above, may be configured to conform to any shape, and may be manufactured with spherical, cylindrical or other desired symmetry.

Suitable activation methods for embodiments of the microposts may be determined by the composition and manufacturing method of the shape memory polymer or alloy used to fabricate the microposts. There are a variety of suitable activation methods for shape memory materials that may be suitable for the embodiments discussed herein. For example, application of thermal energy or the application of mechanical energy in the form of ultrasonic vibrations or the like may be used to activate the microposts. The balloon embodiments previously described are used in FIGS. 12A-14B as exemplary to describe various activation methods which would be applicable to the embodiments described herein.

Figure 12A:
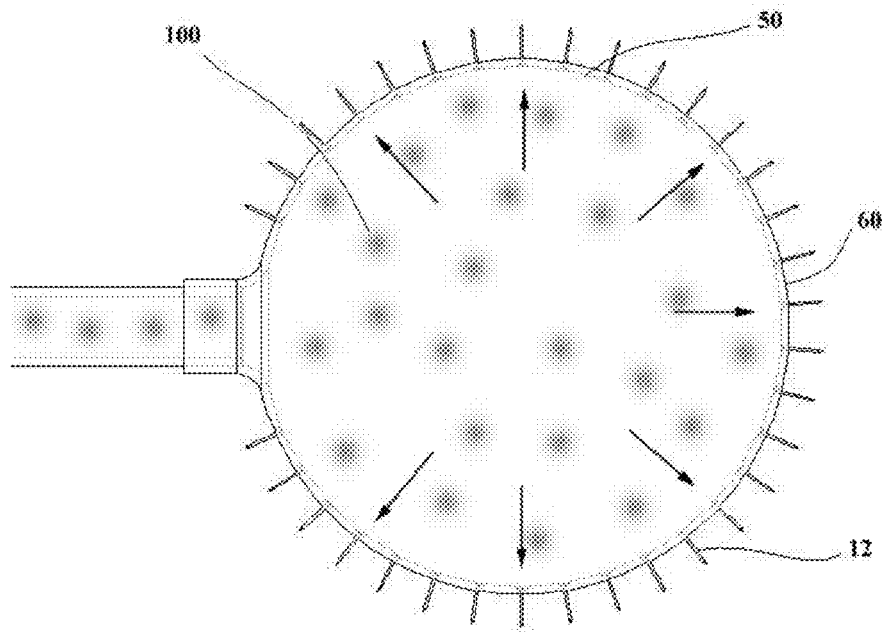
FIGS. 12A and 12B illustrate an embodiment of a balloon device having an array of a plurality of microposts disposed within tissue and transitioning from a deployment state to an engagement state with heat activation.
Figure 12B:
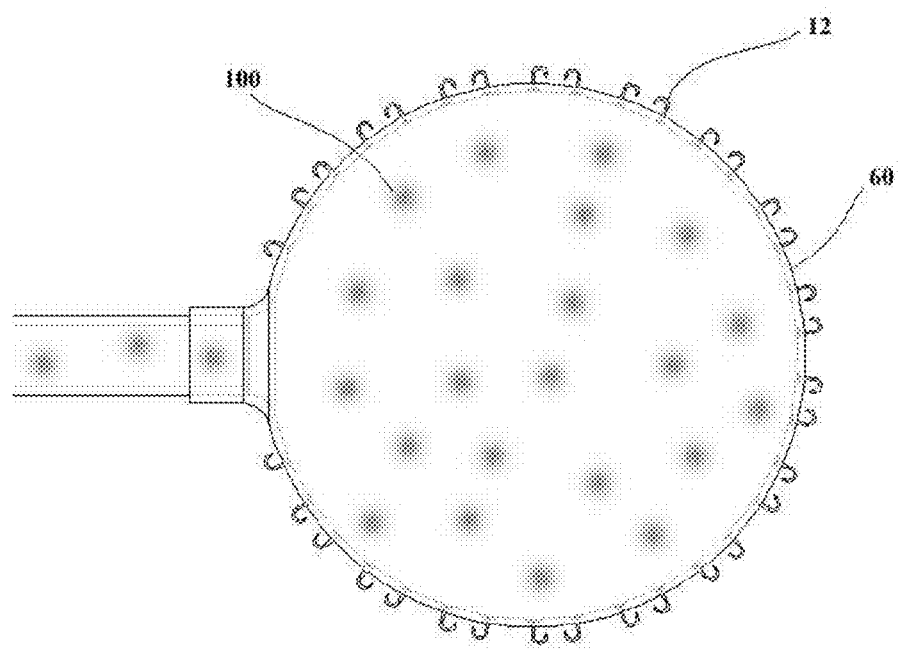

For thermal activation, balloon 60 may be filled with fluid 100 that is at a temperature higher than the shape memory activation temperature of the microposts as shown in FIGS. 12A and 12B. In FIG. 12A, heat 103 is shown being transferred from fluid disposed within the interior of the balloon through the wall of substrate 50 and into the tissue 102 surrounding the embedded microposts extending from the balloon. The elevated temperature of the fluid and surrounding tissue elevates the temperature of the microposts causing them to transition into the engagement state 12' as shown in FIG. 12B.

Shape memory polymers may also be transitioned from the deployment state to the engagement state by a change in the pH value of the material that is surrounding the polymer. For activation by a change in the pH value of the material that surrounds the microposts, the pH level of the tissue may be different enough from that of the blood to activate the microposts after they had been deployed into the tissue. Also, a fluid having an activation pH level may be disposed within fluid communication of the microposts by injection into the balloon interior or any other suitable means.

Figure 13A:
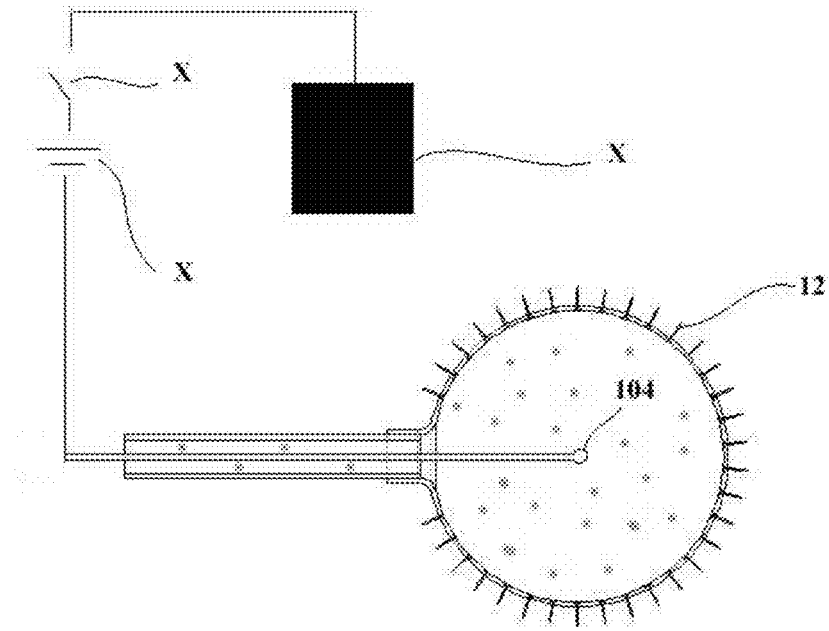
FIGS. 13A and 13B illustrate an embodiment of a balloon device having an array of a plurality of microposts disposed within tissue and transitioning from a deployment state to an engagement state with electrical current activation.
Figure 13B:
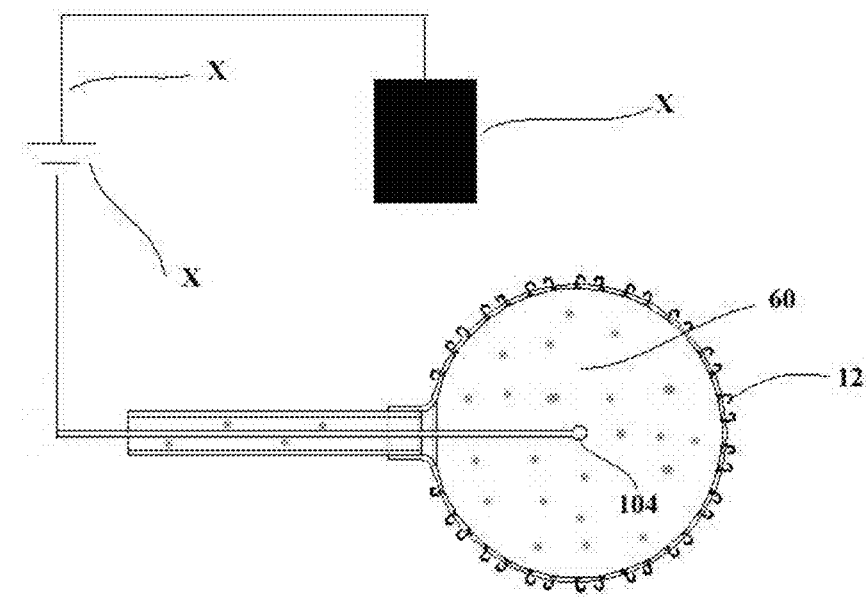

The application of electrical energy may also be used to activate shape memory polymers that have been doped with carbon nanotubes, which make the doped material conductive. FIGS. 13A and 13B illustrate a balloon embodiment with micropost activation by the application of electrical energy. For activation by electrical energy, fluid 104 contained within the balloon 60 may be electrically conductive such as with a saline solution or the like. Electrical current generated by a battery 106 or other appropriate source may then be passed through the fluid via the electrically conductive probe 101 and microposts into an electrical return patch 110 that is placed on the outside of the tissue as illustrated in FIG. 13A. Upon activation of switch 108, the electrical current may be passed through resistive elements, such as carbon nanotubes in the microposts 12, thus heating and activating the microposts transitioning them to the engagement state 12' as shown in FIG. 13B.

Figure 14A:
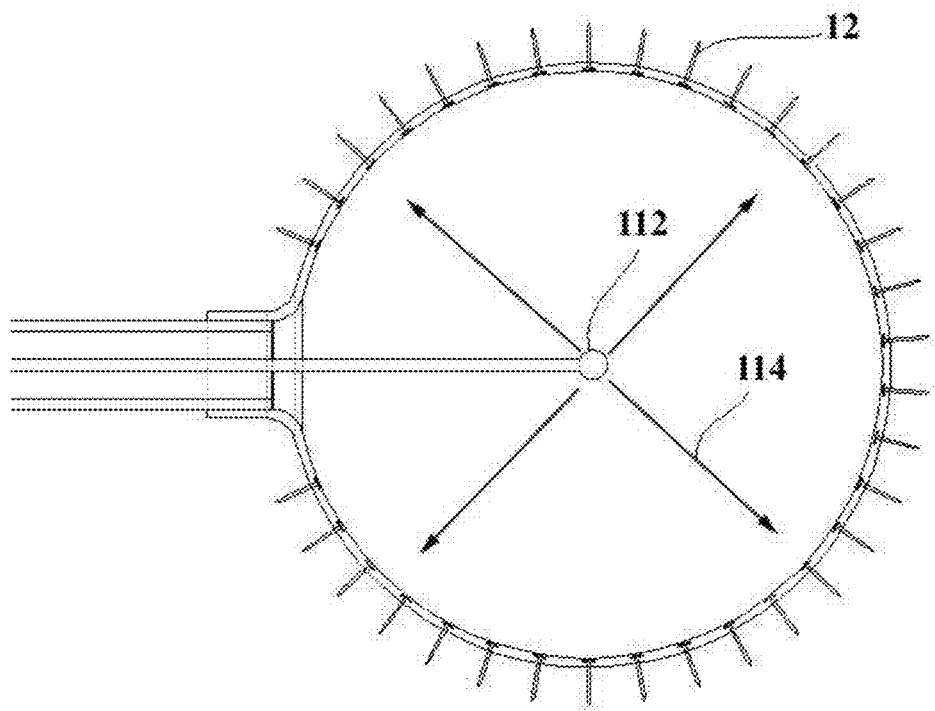
FIGS. 14A and 14B illustrate an embodiment of a balloon device having an array of a plurality of microposts disposed within tissue and transitioning from a deployment state to an engagement state with ultraviolet light activation.
Figure 14B:
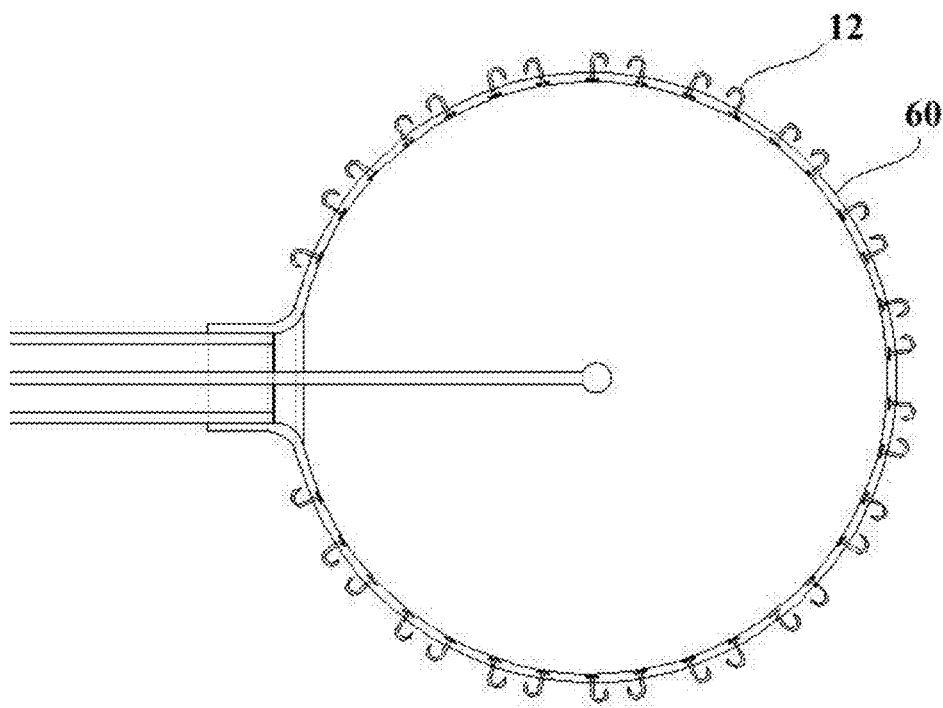
Figure 14C:
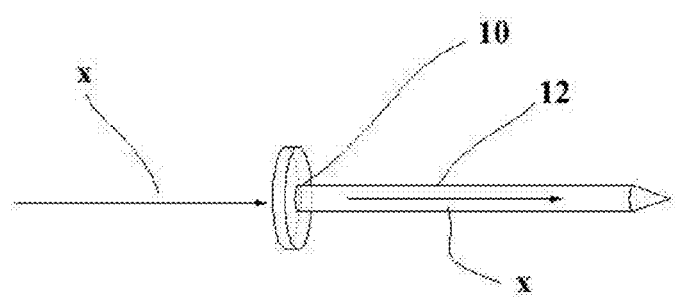
FIG. 14C illustrates the use of the micropost as a waveguide for light transmission during activiation.

It has been shown that the application of light can cause the activation of a shape memory polymer. The shape memory materials can change shape when struck by light at certain wavelengths and return to their original shapes when exposed to light of specific different wavelengths. FIGS. 14A and 14B illustrate a balloon embodiment with micropost activation by photon absorption. In FIG. 14A, a light diffusing element 112 is placed into the interior of the balloon which has been pneumatically or hydraulically inflated. The light diffusing element 112 is then turned on saturating the interior walls of the balloon with photons generally represented by arrows 114. After absorbing sufficient photons, the microposts 12 are engaged as shown in FIG. 14B. As shown in FIG. 14C, the microposts 12 may be configured to function as waveguides, allowing the light to pass from the proximal end 10 to the distal tip 18 of the micropost thus activating the micropost. Light energy may thus be communicated into an interior cavity of the balloon with a fiber optic waveguide and then radiated outwardly towards the spherical shell of the balloon and the proximal ends of the microposts. The light energy may then be transmitted from the proximal ends of the microposts to distal sections of the microposts so as to heat or otherwise activate the microposts as shown in FIG. 14C.

Figure 15:
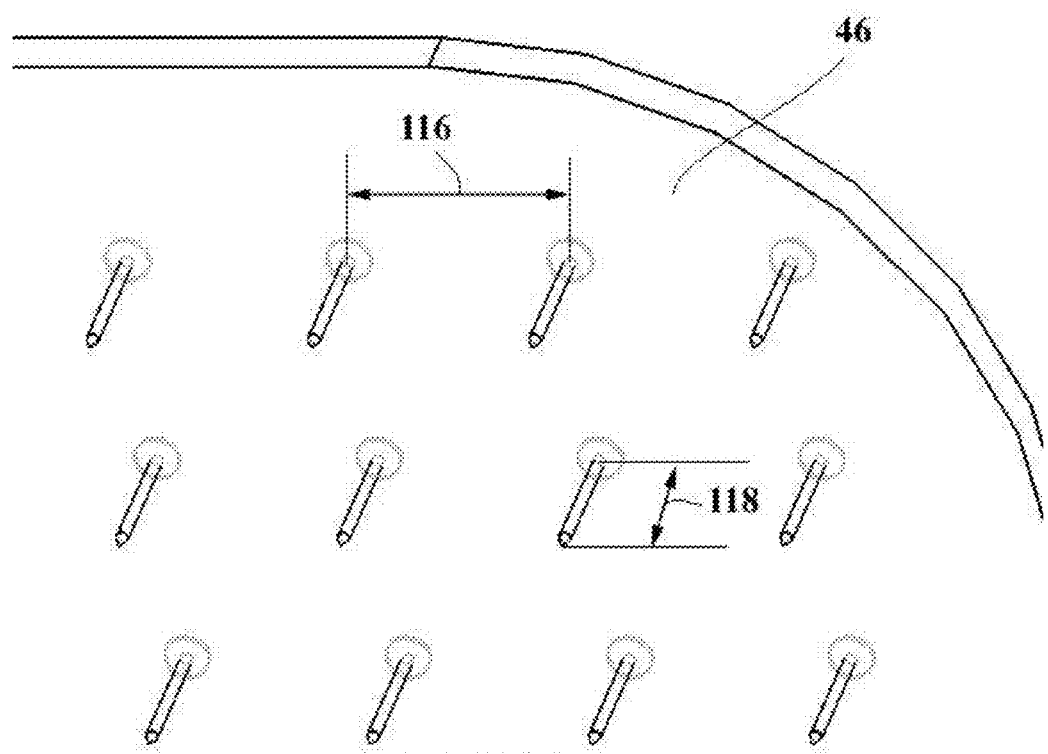
FIG. 15 is a perspective view of a sheet of flexible material with an array of a plurality microposts extending therefrom in a deployment state.

The length and spacing of the microposts may be dependent on the target tissue into which they are being deployed. For some embodiments, the microposts may cause some damage to the cells of the target tissue as they are being deployed. Thus, each micropost may be spaced such that they cause the least amount of damage to the target tissue. FIG. 15 illustrates an array 46 having inter-micropost spacing 116 and 117 of about 8 microns to about 40 microns, and an axial length 118 of about 8 to 20 microns. These spacing and length dimensions may be suitable for target tissue with cells having a mean diameter of about 1 micron to about 2 microns. As previously calculated, the attachment strength for a substrate embedded with shape memory polyurethane microposts that have a Young's modulus value of about 1100 MPa was calculated to be about 20.8 kPa. FIG. 15 demonstrates a uniform spacing of microposts in the array which may be applicable to certain applications. Non-uniform spacing in one or both directions of the array may be employed in alternative embodiments for suitable applications.

The micropost deployment method embodiments discussed above may be applied in reverse order to remove the micropost substrate system from the target tissue by reversing the shape memory property to the original deployment state. Consider the micropost substrate system embodiment depicted in FIGS. 2A-2D. For some embodiments the microposts in FIG. 2D may be transitioned from the activated or engaged state to the deployment state by reversing the shape memory activation method. In the case of microposts fabricated from NiTi shape memory material, the deployment state corresponds to the Martensite phase of the material, and the engaged state corresponds to the Austenite phase of the material. The activation temperature represents the transition temperature between these two phases; in this case the activation temperature is body temperature. When the NiTi microposts are deployed into the target tissue they are above their activation temperature and the NiTi is thus in the Austenite phase. A thermal sink that is lower in temperature than the transition temperature may be applied to the substrate sheet thus lowering the temperature of the tissue surrounding the microposts. After the tissue that surrounds the microposts has reached a temperature that is below its transition temperature, for some embodiments the microposts will revert to their deployment state (FIG. 2C). In the case of NiTi microposts, the temperature change reverts the material to its Martensite or deployment state. The micropost/substrate sheet system can then be removed from the target tissue. Thus the steps outlined in FIGS. 2A-2D can be performed in reverse in order to remove the micropost/substrate sheet system from the target tissue.

Having now described various embodiments of the invention in detail as required by the patent statutes, those skilled in the art will recognize modifications and substitutions to the specific embodiments disclosed herein. Such modifications are within the scope and intent of the present invention as defined in the following claims.

What is claimed is:

1. A tissue adhesion device, comprising:
a substrate having a contact surface; and
an array of microposts extending from the contact surface of the substrate, said microposts fabricated from a shape memory material and having a proximal end secured to the substrate and having a sharpened tissue penetrating distal end, each micropost having a deployment state with the microposts in a substantially straightened configuration extending substantially perpendicular from the substrate and substantially parallel to adjacent microposts during penetration of tissue and an engaged state activated through shape memory transition after penetration wherein a distal section of the micropost engages to mechanically capture tissue adjacent thereto and said microposts are no longer substantially parallel to adjacent microposts and no longer in a straightened configuration.

2. The tissue adhesion device as defined in claim 1 wherein in the engaged state the distal end of each micropost has undergone a shape memory transition to be curved back such that a longitudinal axis of the distal end is at an angle of about 45 degrees to about 180 degrees from a nominal longitudinal axis of the micropost in the engaged state.

3. The tissue adhesion device as defined in claim 1 wherein a radius of curvature is established in a distal section through shape memory transition to the engaged state of about 100 percent to about 50 percent of the axial length of the respective microposts in the deployment state.

4. The tissue adhesion device as defined in claim 1 wherein a distal section of each micropost assumes a corkscrew configuration through shape memory transition to the engaged state to mechanically capture tissue adjacent thereto in the deployed state.

5. The tissue adhesion device as defined in claim 1 wherein the shape memory material is selected from the set of shape memory polymers and shape memory alloys.

6. The tissue adhesion device as defined in claim 5 wherein the shape memory material is a polymer selected from the set of polyurethane, polystyrene, polynorbornene or hydrogels.

7. The tissue adhesion device as defined in claim 5 wherein the shape memory material is NickelTitanium.

8. A tissue adhesion system comprising:
an elastically expandable substrate;
an array of microposts extending from the external surface of the substrate, said microposts fabricated from a shape memory material and having a proximal end secured to the substrate and having a sharpened tissue penetrating distal end with a deployment state with the microposts in a substantially straightened configuration substantially perpendicular to the substrate and substantially parallel to adjacent microposts during penetration of tissue and an engaged state activated through shape memory transition after penetration wherein a distal section of the micropost engages to mechanically capture tissue adjacent thereto and said microposts are no longer substantially parallel to adjacent microposts and no longer in a straightened configuration.

9. The tissue adhesion system as defined in claim 8 wherein the elastically expandable substrate is a balloon.

10. The tissue adhesion system as defined in claim 9 further comprising a catheter shaft removably attached to the substrate for inflation and deflation of the balloon substrate.

11. The tissue adhesion system as defined in claim 9 wherein the balloon substrate includes an internal surface which is self adhering upon deflation.

12. The tissue adhesion system as defined in claim 11 wherein the implantable device is a stent.

13. The tissue adhesion system as defined in claim 8 wherein the elastically expandable substrate is a tube.

14. The tissue adhesion system as defined in claim 8 wherein the elastically expandable substrate is attached as a coating on an implantable device.

15. A method for tissue adhesion comprising
providing a substrate having a contact surface; and
forming an array of microposts extending from the contact surface of the substrate, said microposts fabricated from a shape memory material and having a proximal end secured to substrate, a sharpened tissue penetrating distal end;
deploying the microposts by penetrating into tissue for a desired procedure in a substantially straightened configuration substantially perpendicular to the substrate and substantially parallel to adjacent microposts; and,
engaging the microposts by activation of the shape memory material after penetration wherein a distal section of the micropost mechanically captures tissue adjacent thereto and said microposts are no longer substantially parallel to adjacent microposts and no longer in a straightened configuration.

16. The method for tissue adhesion as defined in claim 15 wherein the desired procedure is an anastomosis and the substrate provided is a flexible tube, the step of deploying comprises
inserting the flexible tube into both sides of an anastomosis connection; and
advancing the tissue penetrating distal ends of an array of microposts extending from and secured to a contact surface of the outer surface of the flexible tube into target tissue in both sides of the anastomosis connection.

17. The method for tissue adhesion as defined in claim 15 wherein the desired procedure is an insertion of an implantable device, the step of providing a substrate comprises attaching the substrate as a coating on the implantable device and the step of deploying includes
inserting the implantable device in a target area adjacent tissue to be engaged and
advancing the tissue penetrating distal ends of the array of microposts extending from and secured to the coating on the outer surface of the implantable device into target tissue.

18. The method for tissue adhesion as defined in claim 17 wherein the implantable device is a stent.

19. The method for tissue adhesion as defined in claim 15 wherein the desired procedure is closure of a wound and the substrate is provided as a flexible balloon, the step of deploying comprising
inserting the balloon into a wound;
expanding the balloon such that the microposts are expanded radially outward towards the extent of the wound in the target tissue and the tissue penetrating tips of the microposts penetrate the target tissue;
and after the step of engaging, further comprising collapsing the balloon to draw the wound closed.

\* \* \* \* \*